United States Patent [19]

Lamport et al.

[11] Patent Number: 5,681,328

[45] Date of Patent: Oct. 28, 1997

[54] RECIPROCATING SERIAL TRANSPARENT ELASTIC BAND LIGATOR

[75] Inventors: Ronald B. Lamport, Pelham; Thomas E. Watson, Hooksett, both of N.H.

[73] Assignee: C.R. Bard, Inc., Murray Hill, N.J.

[21] Appl. No.: 700,424

[22] PCT Filed: Dec. 20, 1994

[86] PCT No.: PCT/US94/14796

§ 371 Date: Nov. 20, 1996

§ 102(e) Date: Nov. 20, 1996

[87] PCT Pub. No.: WO96/19145

PCT Pub. Date: Jun. 27, 1996

[51] Int. Cl.⁶ ................................. A61B 17/00
[52] U.S. Cl. ................................. 606/140
[58] Field of Search .................... 606/139–141, 606/148, 151

[56] References Cited

U.S. PATENT DOCUMENTS

| | | |
|---|---|---|
| 3,760,810 | 9/1973 | Van Hoorn . |
| 3,985,138 | 10/1976 | Jarvik . |
| 4,226,239 | 10/1980 | Polk et al. . |
| 4,860,746 | 8/1989 | Yoon . |
| 5,203,863 | 4/1993 | Bidoia . |
| 5,207,690 | 5/1993 | Rohrabacher et al. . |
| 5,269,789 | 12/1993 | Chin et al. . |
| 5,320,630 | 6/1994 | Ahmed .................. 606/140 |
| 5,356,416 | 10/1994 | Chu et al. .................. 606/140 |

Primary Examiner—Gary Jackson
Attorney, Agent, or Firm—Darby & Darby

[57] ABSTRACT

A ligating band dispenser for dispensing a plurality of ligating bands having located at the distal end of an elongated introducer responds to manipulation of an operating structure at the proximal end of the introducer. It has a spring loaded reciprocating inner cylinder movable within a spring loaded, radially expandable cone having inner teeth for engaging a plurality of ligating bands. When the dispenser is actuated, the inner cylinder us drawn proximally with respect to the cone, and the distal end surface of the cone forces the distal-most ring off the reciprocating cylinder and onto the internal tissue has been drawn or place by the inside cylinder.

15 Claims, 5 Drawing Sheets

RECIPROCATING SERIAL TRANSPARENT ELASTIC BAND LIGATOR

FIELD OF THE INVENTION

This invention generally relates to ligating instruments and more particularly to instruments for dispensing a plurality of ligating bands to one or more internal sites within a patient's body in a single ligation procedure, without removing the instrument between successive ligating band placements.

BACKGROUND OF THE INVENTION

Brief Description of Related Art

The treatment of various types of lesions including internal hemorrhoids by ligation is well known. The object of ligation is to position an elastic cord, or ligating band, at the lesion to stop circulation through tissue and allow the tissue to necrose whereupon the body sloughs off the necrotic or dead tissue.

Surgical ligation has also been employed in female and male sterilization procedures. In the case of tubal ligation in female patients, ligating rings or bands are placed on a folded-over loop portion of each Fallopian tube, blocking the path from uterus to ovaries, and thereby preventing fertilization of an ovum. In the case of male sterilization, a ligating band may similarly be placed on a folded-over loop portion of the vas deferens, thus preventing passage of spermatozoa from the testes.

The following U.S. Pat. Letters Nos. disclose various embodiments of ligating instruments: 3,760,810 to Van Hoorn; 4,257,419 to Goltner, et al.; and 4,735,194 to Stiegmann.

U.S. Pat. No. 3,760,810 to Van Hoorn discloses an instrument for facilitating the placement of a single ligating band or set of bands. The instrument includes, at its distal end, a ligating band dispenser comprising two rigid, concentric tubes. The tubes can slide with respect to each other under the control of a trigger mechanism at the proximal end of the instrument. A rigid endoscope having internal passages forming a suction path and a light path interconnect the trigger mechanism and dispenser. The inner tube can be loaded with a set of one or more elastic rings or ligating bands. A separate stopper bar attaches to the instrument to prevent premature dispensing. When the instrument is located proximate a lesion, a surgeon removes the stopper bar and applies vacuum to draw tissue into a hollow passage at the distal end of the instrument. Pulling on the trigger retracts the inner tube. A radial surface or shoulder on the outer tube engages the ligating band so it can not displace with the inner tube. As the inner tube is withdrawn from the ligating band, it collapses onto the tissue.

U.S. Pat. No. 4,257,419 to Goltner, et al. discloses a rigid endoscope that includes a ligating band dispenser with an inner tube that moves with respect to an outer tube to dispense a ligating band. This dispenser is oriented at right angles to the rigid endoscope and includes a structure for moving the inner tube of the dispenser in this configuration.

U.S. Pat. No. 4,735,194 to Stiegmann discloses a flexible endoscope ligating instrument in which a flexible endoscope structure includes a biopsy channel and a suction channel extending between the proximal and distal ends. A dispenser, like the dispenser structure shown in the Van Hoorn and Goltner patents, includes an inner tube that moves axially with respect to an outer tube at the distal end of the instrument. The outer tube connects to the distal end of the endoscope. An operating mechanism in the form of a pull wire with a weighted handle maintains tension on the inner tube so it does not displace axially outward while the instrument is being positioned. For some applications it is suggested that the endoscope structure be inserted through an overtube to prevent premature dispensing. Suction can be applied to draw tissue into a central aperture of the dispenser. Then a surgeon pulls the handle and retracts the inner tube axially past the distal end of the outer tube to force the ligating band off the instrument onto the tissue.

Each of the foregoing instruments dispenses a single ligating band or a single set of ligating bands at a single location. None of the patents suggests dispensing ligating bands at discrete locations. The Van Hoorn patent does disclose the possibility of depositing plural ligating bands. However, Van Hoorn seems only to suggest dispensing plural ligating bands at a single site in a single operation. The apparatus disclosed in the Van Hoorn, Goltner or Stiegmann patents apparently would have to rely on a surgeon's sense of touch in order to displace the inner tube by an incremental distance corresponding to the thickness of a stretched ligating band to deposit a plurality of bands at different sites. That would be very difficult to accomplish.

With the foregoing described devices, when it is desired to deposit ligating bands at different sites, the common practice was to withdraw the entire instrument from the patient and load a new ligating band onto the inner tube. Loading ligating bands on an instrument requires special tools and could be time consuming particularly if the special tooling must be retrieved to install each ligating band individually while the instrument is withdrawn. Each of these instruments requires some structure, such as special stoppers or overtubes, for preventing the premature dispensing of the ligating band. Consequently, none of these instruments was readily adapted for dispensing ligating bands at different sites without withdrawing the instrument after each individual site is ligated.

Aimed at solving the aforementioned problems, the following U.S. Pat. Nos. disclose various embodiments of ligating instruments which are designed to deposit or place a plurality of ligating bands at one or more internal sites within a patient without the necessity of withdrawing the ligating instrument to reload successive ligating bands: 3,985,138 to Jarvik; 4,226,239 to Polk et al.; 3,870,048 to Yoon; 5,207,690 to Rohrabacher et al.; and 5,269,789 to Chin.

U.S. Pat. No. 3,985,138 to Jarvik discloses a ligature gun for placing a plurality of preformed suture loops which are tightened around bleeders after emplacement. The successive preformed suture loops are advanced to the dispensing end of the ligature gun by rotation of a threaded rod onto which the loops have been preloaded. The Jarvik ligature gun comprises large number of mechanical parts and is relatively complex in design and operation.

U.S. Pat. No. 3,870,048 to Yoon discloses the use of elastic bands or rings in tubal ligation. The Yoon device is constructed so as to permit two or more ligating rings to be loaded at the same time, but discharged separately at different times and in succession to one another, even at different locations, all without removing the ligating device from the patient's body cavity. Yoon's device is also relatively complex.

U.S. Pat. No. 4,226,239 to Polk et al. also describes a surgical ligating instrument for tubal ligation within a human or animal body, by the application of two or more elastic ligating rings without the necessity of removing the instrument from the patient for each ligating ring. In the device of Polk et al., a number of ligating rings are stretched over a cylindrical shaft which is slidably and concentrically received within an outer cylindrical sleeve. As the cylindrical shaft is withdrawn proximally with respect to the outer sleeve, the outer sleeve successively forces the ligating rings off of the shaft, preferably one at time. The extent of relative motion between the shaft and the sleeve is controlled by a mechanical stop at the proximal end of the shaft, located in the pistol handle of the instrument. The surgeon can be sure that a only single band has been placed only if the mechanical stop is precisely calibrated to the width of an individual ligating ring. U.S. Pat. No. 4,860,746 discloses a device similar to that of Polk et al.

U.S. Pat. No. 5,207,690 to Rohrabacher et al. teaches that successive ligating rings may be slipped off of the cylindrical shaft onto which they have been preloaded by the use of separate forceps.

U.S. Pat. No. 5,269,789 to Chin discloses a ligating band dispenser located at the distal end of an elongated introducer, which dispenser responds to manipulation of an operating structure at the proximal end of the introducer. The dispenser comprises first and second coaxially located, interfitted segments that support ligating bands at a plurality of axially spaced positions thereon. Each segment includes a spaced ligating band engagement structure for engaging portions of each ligating band or set of bands. One of the segments connects to the operating structure for being moved between first and second positions relative to the other of the segments. This motion dispenses one of the ligating bands from the distal end of the ligating instrument and moves the remaining ligating bands distally with respect to the dispensing means thereby to position a successive ligating band for being dispensed at a different site, as in some of the aforementioned devices as well. The Chin et al. instrument, however, is an improvement over those devices in that it is specially constructed to prevent more than a single ligating band from being dispensed in response to a single actuation of the operating structure. On the other hand, the ligating bands are initially greatly stretched when loaded onto the Chin et al. instrument, bringing about the necessity of a relatively strong spring in order to slide the bands distally. The surgeon's hand must work against this spring when actuating the device. Moreover, advancement of the ligating bands toward the dispensing end of the device requires the bands to be stretched even further than their initial stretched conditions. Such stretching requires even greater force to applied by the surgeon's hand.

OBJECTS AND SUMMARY OF THE INVENTION

Therefore, it is an object of this invention to provide an instrument that can dispense plural ligating bands in sequence at discrete sites.

Another object of this invention is to provide a ligating instrument that can deposit plural ligating bands in sequence without requiring the instrument to be removed from a patient after each ligation.

Still another object of this invention is to provide a ligating band dispenser for attachment to diverse introducer structures including rigid and flexible endoscopes for ligating tissue.

Still another object of this invention is to provide a dispenser for attachment to a ligating instrument that dispenses plural ligating bands at different locations, that is reliable and easy to use and that inherently prevents any premature dispensing of the ligating band during instrument positioning.

A further object of this invention is to achieve all of the foregoing objects in a device which is especially easily actuable or, in other words, which does not require significant hand strength for its successful operation, either in dispensing or advancing successive ligating rings.

Yet still another object of this invention is to provide an improved method for applying multiple ligating bands at discrete sites without having to withdraw a ligating instrument after each ligation, and which method avoids the use of large forces in applying the bands.

In accordance with one embodiment of this invention, a ligating band dispenser located at the distal end of an elongated introducer responds to manipulation of an operating structure at the proximal end of the introducer. The dispenser comprises a spring loaded, reciprocating inner cylinder movable within a spring loaded, radially expandable cone having inner teeth for engaging a plurality of ligating bands. The cone is comprised of four arcuate fingers, each spanning an arc of about 90 degrees. The fingers are normally biased by small flat springs towards and into engagement with the reciprocating inner cylinder, with each ligating band being positioned distally of a respective inner tooth on the inside of the finger. When the dispenser is actuated, the inner cylinder is drawn proximally with respect to the cone, and the distal end surface of the cone forces the distal-most ring off of the reciprocating cylinder and onto whatever internal tissue has been drawn or placed inside the cylinder. In addition, the remaining ligating bands are also moved distally on the reciprocating cylinder by respective distal-facing end surfaces of the inwardly protruding teeth on the arcuate fingers forming the cone. After the ring has been dispensed, a coil spring forces the inner cylinder distally again with respect to the cone. As this occurs, the cone segments or fingers are splayed or moved radially outwardly, against the force of the small flat biasing springs, as ramped surfaces on the proximal sides of all of the teeth come into contact with the remaining ligating bands. The teeth then "ratchet" over the bands, with the distal-most band being placed in front of the distal end surface of the cone, and thus in position for delivery as desired at a different internal body site. The spring forces exerted inwardly by the small flat springs are balanced against the coil spring which causes the reciprocating inner cylinder to travel distally, as well as against the frictional forces exerted by the ligating bands on the reciprocating cylinder itself. By so doing, only a very small spring force for the coil spring is required, thus minimizing the forces against which the surgeon must act in order to operate the instrument safely and efficiently.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DETAILED DESCRIPTION OF A PREFERRED EMBODIMENT

Figure 1:
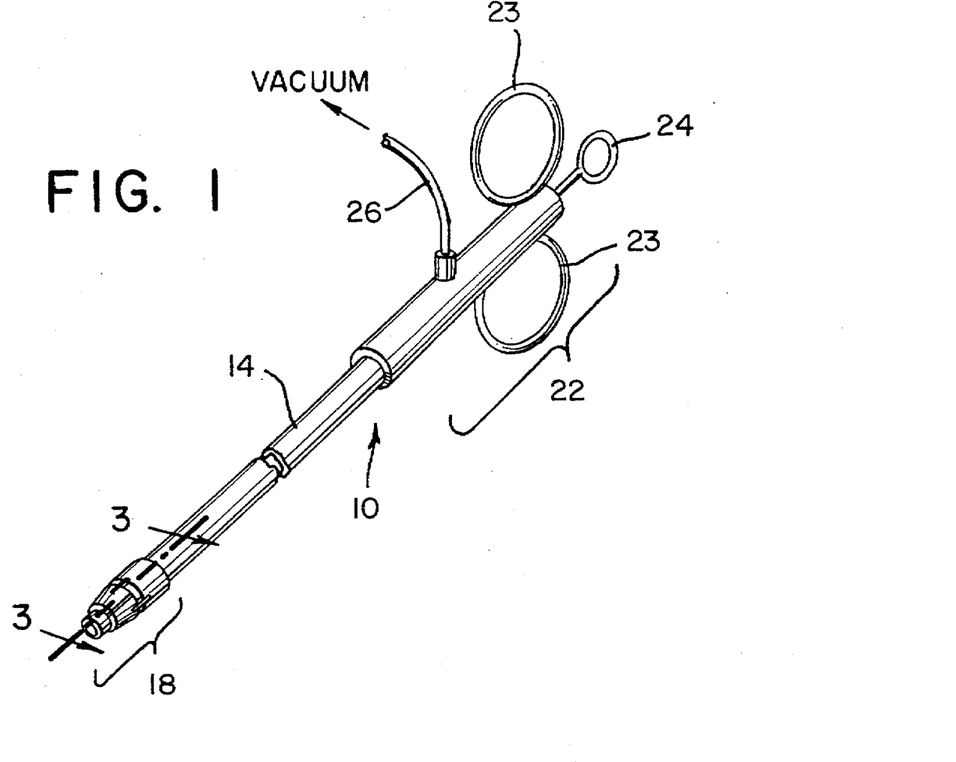
FIG. 1 depicts one embodiment of a ligating instrument constructed in accordance with this invention.

FIG. 1 depicts, in perspective view, one embodiment of a ligating instrument that serially dispenses elastic ligating bands during a succession of operations. The ligating instrument 10 generally includes an introducer in the form of an elongated, rigid tubular housing 14. A proximal end portion 22 of the instrument 10 comprises a handle 23 for manipulation by a surgeon, and a dispensing actuator or trigger 24 for causing a ligating band to be dispensed by the instrument 10. The housing 14 is formed in a hollow tubular form to provide a central or axial passage that communicates a vacuum connection 26 connected to the proximal end portion 22 with the distally mounted ligature dispenser 18, as will be explained in greater detail below.

The trigger 24 attaches to a pull or trip wire that passes through a proximal seal (not shown) located within the proximal end portion 22 of the instrument 10, and which connects to the dispenser 18. Variations of such a trigger and pull wire operating structure have been incorporated in ligating instruments. The specifically disclosed embodiment is merely representative of such diverse implementations.

The proximal seal referred to above allows suction to be applied by the vacuum connection 26 and the central passage of the instrument to and through the dispenser 18, while allowing reciprocal motion of the trip wire. With such a proximal seal in place, suction applied to the vacuum connection 26 draws tissue into the dispenser 18 for ligation, as will be made clear below.

While a specially designed ligating instrument 10 has been illustrated, it will be readily apparent to those of ordinary skill in the relevant art that the dispenser 18 may be connected, such as by a friction fit, to the end of a conventional endoscope having a central lumen therethrough and access ports at the proximal working end to permit the application of suction and the passage of a trip wire externally of the endoscope handle. In such a case, the surgeon may simply pull on the trip wire itself to deliver a ligating ring, or she may attach a clamp of any suitable kind to the wire, for ease of manipulation. None of these differences affects the scope of the present invention, which is directed to the construction and operation of dispenser 18 itself.

The ligating instrument 10 or a conventional endoscope may further include means for providing visualization of internal body tissue distal of the dispenser 18, such as a conventional fiber optic and lens arrangement (not shown) or the like. In use, such visualization means generally assists the surgeon in guiding the dispenser 18 to the desired tissue site to be ligated.

Figures 2, 5:
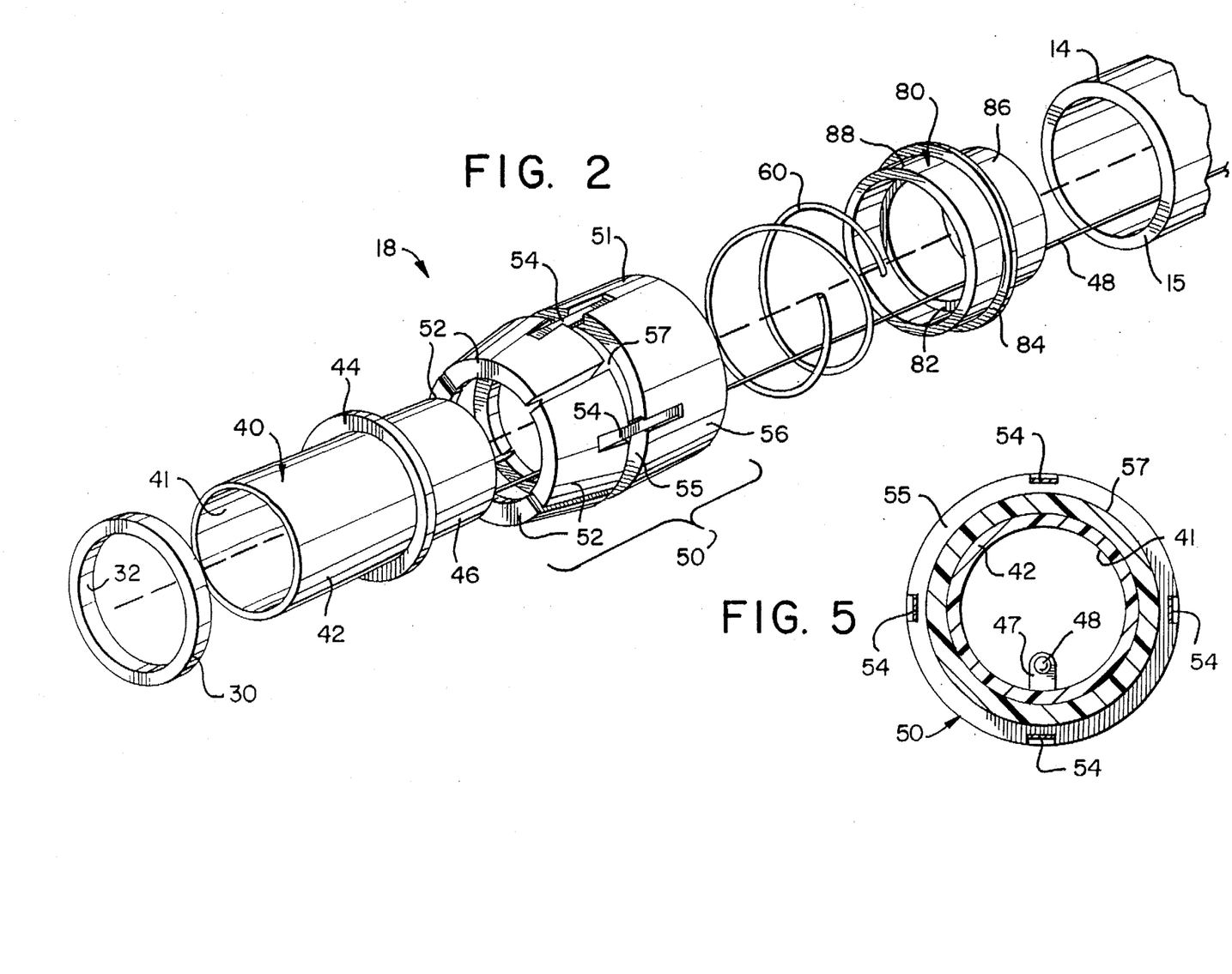
FIG. 2 is a partially exploded perspective view of one embodiment of a ligating instrument dispenser constructed in accordance with this invention.
FIG. 5 is a cross sectional view taken along line 5—5 in FIG. 3.

Referring generally to FIGS. 2 though 6, in which like component parts are consistently numbered for ease of reference, the component parts and manner of assembly thereof to provide the dispenser 18 of the ligating instrument 10 of FIG. 1 are shown in detail.

Referring now to FIG. 2, the component parts of dispenser 18 are shown in partially exploded view. Proceeding from left to right in the figure, a ligating band 30, preferably formed of isoprene, is a circular ring having a generally square solid body cross-section. So formed, the ring or band 30 has a flat, smooth inside surface 32 for mounting on reciprocating inner cylinder 40, which is preferably formed of substantially transparent polycarbonate. In use, a plurality of ligating bands 30 will be initially positioned on the distal portion 42 of inner cylinder 40. Inner cylinder 40, like all other components of the instrument 10, includes a hollow central passage 41 for the application of suction at the distal end of the device. Reciprocating inner cylinder 40 carries an integral outer flange 44 and includes a proximal section 46, the purpose and function of which will be explained in more detail below.

Moving further to the right in FIG. 2, spring finger assembly 50 comprises distal cap 51 and a plurality of arcuate, multi-fire spring fingers 52. In the embodiment shown, there are four such spring fingers 52, each spanning an arc of approximately 90 degrees. Each arcuate multi-fire spring finger 52 is connected to the distal cap 51 by a flat finger spring 54 which biases the respective spring fingers 52 radially inwardly. The spring fingers 52, flat springs 54 and distal cap 51 may be adhesively joined to one another, or may be insert molded in conventional manner. In addition, it is contemplated that the entire spring finger assembly 50 may be integrally injection molded and made of a single material such as substantially transparent polycarbonate, including the flat finger springs 54.

Distal segment 57 of distal cap 51 has reduced outer diameter as seen from outer annular land 55.

It should be noted that the inner cylinder 40 and spring finger assembly 50 are shown in FIG. 2 reverse order of assembly for the sake of clarity, in order to represent that ligating band 30 mounts onto the distal portion 42 of reciprocating inner cylinder 40. In practice, inner cylinder 40 is positioned between spring finger assembly 50 and return coil spring 60, as will be evident from the further figures and detailed description.

Figure 3:
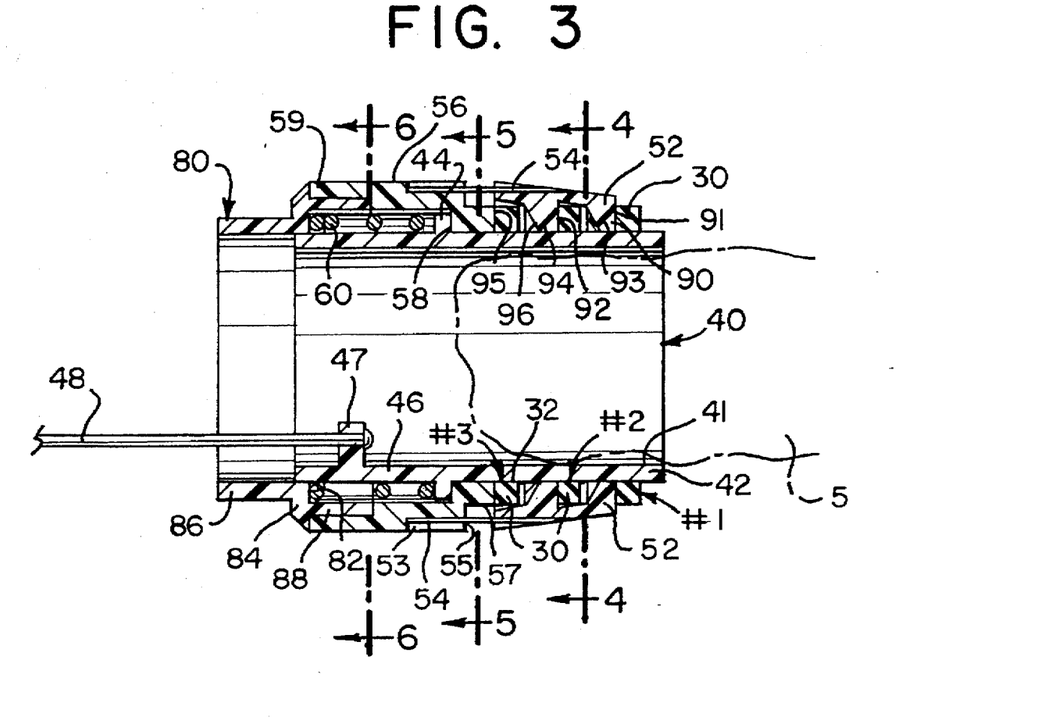
FIG. 3 is a cross sectional view of the embodiment of FIG. 2, taken along line 3—3 in FIG. 1, showing the device in assembled form and in a fully loaded state immediately prior to placement of a ligating band.

Return coil spring 60, preferably formed of 0.020 inch diameter music wire, is mounted onto proximal portion 46 of reciprocating inner cylinder 40, and resiliently biases inner cylinder 40 in a distal direction within spring finger assembly 50 and toward internal distal annular land 58, as seen in FIG. 3. Such biasing action is occasioned by enclosing the distal end of return coil spring 60 within proximal cap 80 and against annular coil spring seat 82, as best seen in FIGS. 2 and 3. Referring specifically to FIG. 3, it can be seen that reciprocating tuner cylinder 40 travels between a first position in which return coil spring 60 is fully extended within the confines of proximal cap 80 and spring finger assembly 50, and a second position in which return coil spring 60 is fully compressed in the proximal direction.

Proximal cap 80 is mounted to the distal end 15 of tubular housing 14 of the ligating instrument 10, or to a similar end of an endoscope. Finally, passing proximally from an attachment lug 47 integrally formed inside inner cylinder 40, a trip wire 48 connects the dispenser 18 to the proximal end of the instrument 10 for manipulation by the surgeon.

Figure 4:
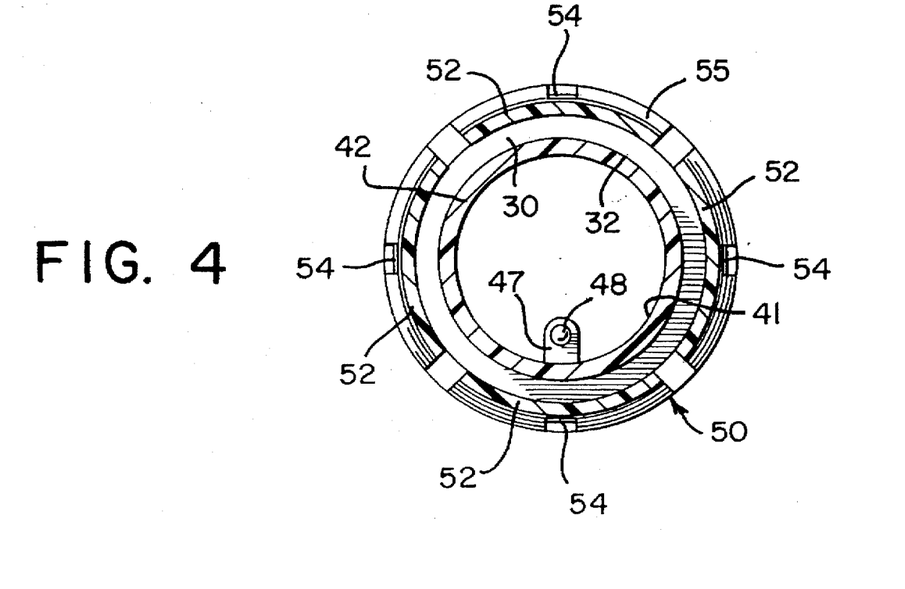
FIG. 4 is a cross sectional view taken along line 4—4 in FIG. 3.
Figure 6:
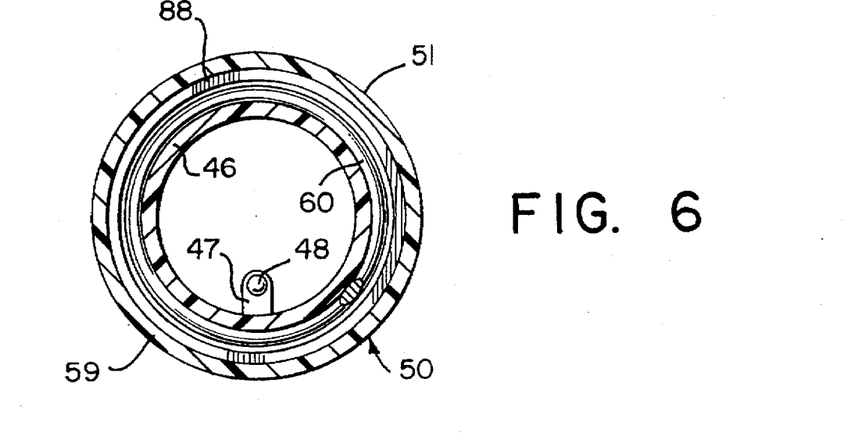
FIG. 6 is a cross sectional view taken along line 6—6 in FIG. 3.

Referring now to FIG. 3, and also simultaneously to cross-sectional views shown in FIGS. 4, 5 and 6, dispenser 18 is shown in its assembled, fully loaded and initial state of operation. Tubular housing 14 of the ligating instrument 10 is not shown, for the sake of clarity. In practice, proximal cylindrical portion 86 of proximal cap 80 is frictionally engaged within tubular housing 14, with the distal end face 15 of tubular housing 14 abutting against annular mounting stop 84. Alternatively, cap 80 and housing 14 may be secured together by other means, for example, an adhesive. Proximal cap 80 further comprises cylindrical mating portion 88 for fitting within and mating to corresponding cylindrical mating portion 59 of distal cap 51.

Both distal cap 51 and proximal cap 80 are preferably formed of substantially transparent polycarbonate.

Arcuate spring fingers 52 are rigidly attached to one end of each of flat finger springs 54 by an adhesive such as cyanoacrylate. As previously noted, springs 54 may be insert molded as well. Similarly, the other ends of each of flat finger springs 54 are adhesively joined into grooves 53 formed in the outer circumference 56 of distal cap 51. In this presently preferred embodiment, the finger springs are formed of 302 stainless steel, have dimensions of 0.050 inch wide by 0.350 inch long by 0.0050 inch thickness, and there are four such finger springs 54. An advantage of this preferred construction and use of such finger springs 54 is that the dispenser 18 is relatively short in its overall axial dimension.

In the relaxed or initial condition shown in FIG. 3, finger springs 54 resiliently urge fingers 52 radially inwardly so as to contact distal portion 42 of reciprocating inner cylinder 40.

Referring to spring fingers 52 more specifically, it is seen that each finger 52 includes two arcuate "teeth" 90 and 94 which protrude radially inwardly toward reciprocating inner cylinder 40. Each tooth 90 and 94 has a flat distal-facing surface 91 and 92, respectively, and a ramped or proximally sloped proximal-facing surface 93 and 96, respectively, the significance of which will become apparent. Distal cap 51 is also provided with a flat, distal-facing surface 95. In the initial, fully loaded condition, each of flat surfaces 91, 92 and 95 abuts against a proximal flat surface of a ligating ring 30 (no. 1, no. 2 and no. 3, respectively). Ligating ring no. 1 is positioned on distal portion 42 of reciprocating inner cylinder 40, distal of the first or distal-most tooth 90 of spring fingers 52. Ligating ring no. 2 is similarly positioned with respect to the other or second tooth 94, more proximally located, of spring fingers 52. Finally, ligating ring no. 3 shown in FIG. 3 is positioned abutting flat surface 95 of proximal cap 80.

In order to place a ligating band on a varix 5 or internal hemorrhoid or other internal body structure, as the case may be, the distal end of the instrument is positioned adjacent such tissue. Because each of reciprocating inner cylinder 40, distal cap 51 and proximal cap 80 is made of a substantially transparent plastic material, in this preferred embodiment, a wide field of view is afforded when the ligating instrument 10 or endoscope includes conventional viewing optics. If these component parts were not transparent, a "tunnel vision" effect would be noticeable to the surgeon due to the fact that the dispenser 18 extends beyond the distal end 15 of tubular housing 14, or beyond the end of the conventional endoscope. Suction is then applied via vacuum connection 26. In this way, the tissue 5 to be ligated is drawn within central bore 41 of the dispenser 18 as shown in dotted lines in FIG. 3. In this position, the instrument may be actuated to place a ligating ring 30 (first ligating ring no. 1) on the tissue to achieve ligation, as will now be explained with reference to FIG. 7.

Figure 7:
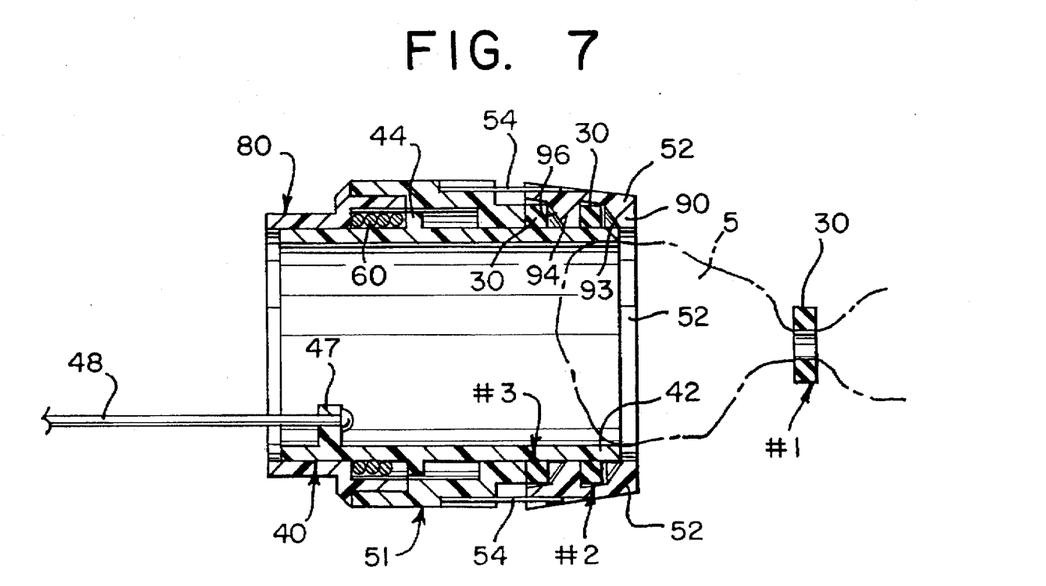
FIG. 7 is similar to FIG. 3, now showing the device in a fully actuated state and immediately after delivery of a ligating band, but prior to relaxation of the coil spring.

Referring now to FIG. 7, dispenser 18 is seen as shown in FIG. 3, but after trip wire 48 has been drawn proximally to compress return coil spring 60 to its fully compressed position. Return coil spring 60 is compressed by flange 44 on reciprocating inner cylinder 40 as inner cylinder 40 is drawn proximally via trip wire 48 and lug 47, as shown. As reciprocating cylinder 40 travels proximally, ligating ring no. 1 is forced relatively distally off of distal portion 42 of inner cylinder 40, and thus onto or over the tissue 5 and thereby accomplishing ligation thereof. At the same time, ligating ring no. 2 and ligating ring no. 3 are also advanced relatively distally on distal portion 42 of reciprocating inner cylinder 40, by a distance equal to the throw of inner cylinder 40 travelling within distal cap 51 and proximal cap 80. Due to the initially loaded condition, as well as the particular construction of spring fingers 54, the surgeon is assured that only a single ligating ring has been dispensed by dispenser 18 of the ligating instrument 10.

Figure 8:
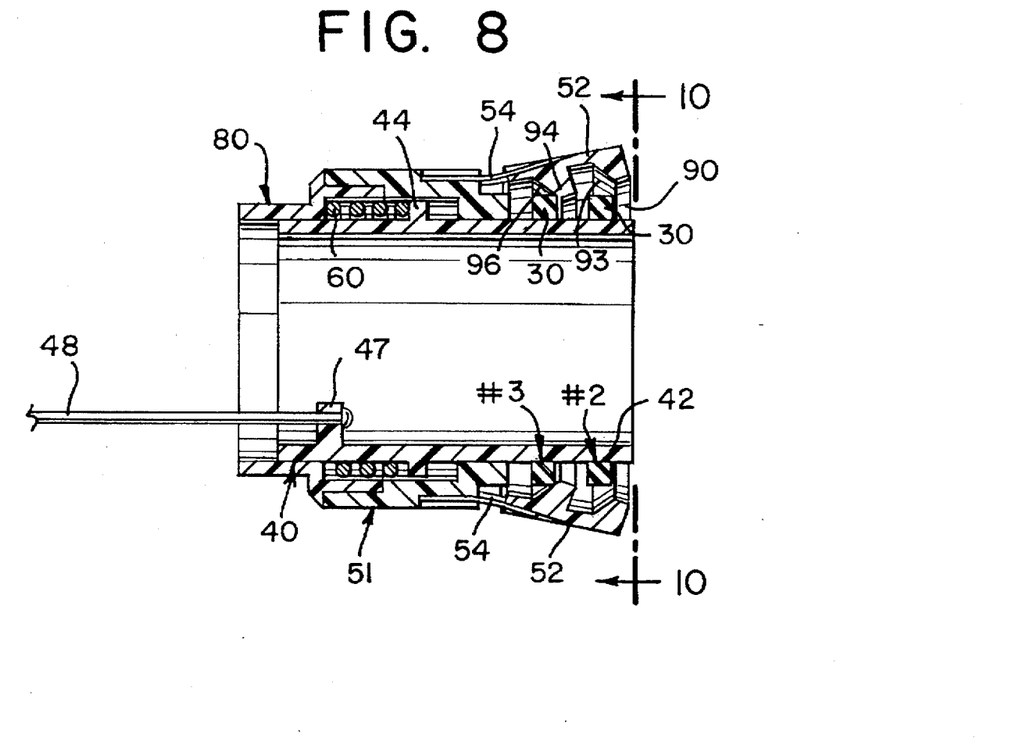
FIG. 8 is similar to FIG. 7, now showing the device in an intermediate position after delivery of a ligating band and during relaxation of the coil spring, and showing splaying of the fingers.

Referring to FIG. 8, dispenser 18 is shown in an intermediate or transient position during return of reciprocating inner cylinder 40 to its distal-most position, under the resilient biasing force of return coil spring 60. Ligating ring no. 1 has been previously dispensed in this figure. As is illustrated, spring fingers 52 are splayed outwardly by virtue of remaining ligating band 30 (ring no. 3) moving distally against ramped surface 96 of proximal tooth 94 of each spring finger 52. The material and dimensions of flat finger springs 54 have been specially selected so as to permit such splaying or outward radial deflection of spring fingers 52 to occur, without permitting ligating band no. 3 to be moved proximally on distal portion 42 of reciprocating inner cylinder 40, as inner cylinder 40 moves relatively distal with respect to spring fingers 52. The presently preferred outside diameter of distal portion 42 of reciprocating inner cylinder 40 is 0.410 inches. The presently preferred dimensions of ligating band 30 for use with the aforesaid inner cylinder 40 are as follows: 0.188 inch outer diameter, 0.063 inch inner diameter, 0.063 inch thickness.

When the presently preferred device is constructed according to the dimensions stated herein, only a relatively light spring 60 is required to return inner cylinder 40 to its distal-most, relaxed position. Thus, the surgeon need only counteract the force of this mild coil spring 60 when actuating the trip wire 48. Of course, the surgeon must also overcome the frictional forces between the remaining ligating bands 30 and the outer surface of distal portion 42 of reciprocating inner cylinder 40. It is believed that the necessity of overcoming these frictional forces is common to every known ligating device of this general type. According to the present invention, however, these frictional forces constitute a substantial majority of the force which must be overcome by the surgeon to actuate the device, in distinction to such prior art devices such as that shown in U.S. Pat. No. 5,269,789 to Chin, et al., in which the user must apply sufficient force to further expand the ligating rings each time the trip wire is pulled.

Returning to FIG. 8, it will be appreciated that as inner cylinder 40 continues to move distally with respect to spring fingers 52, ligating band no. 2 will move to a position distal of the first or distal-most tooth 90 of the spring fingers 52

Figure 9:
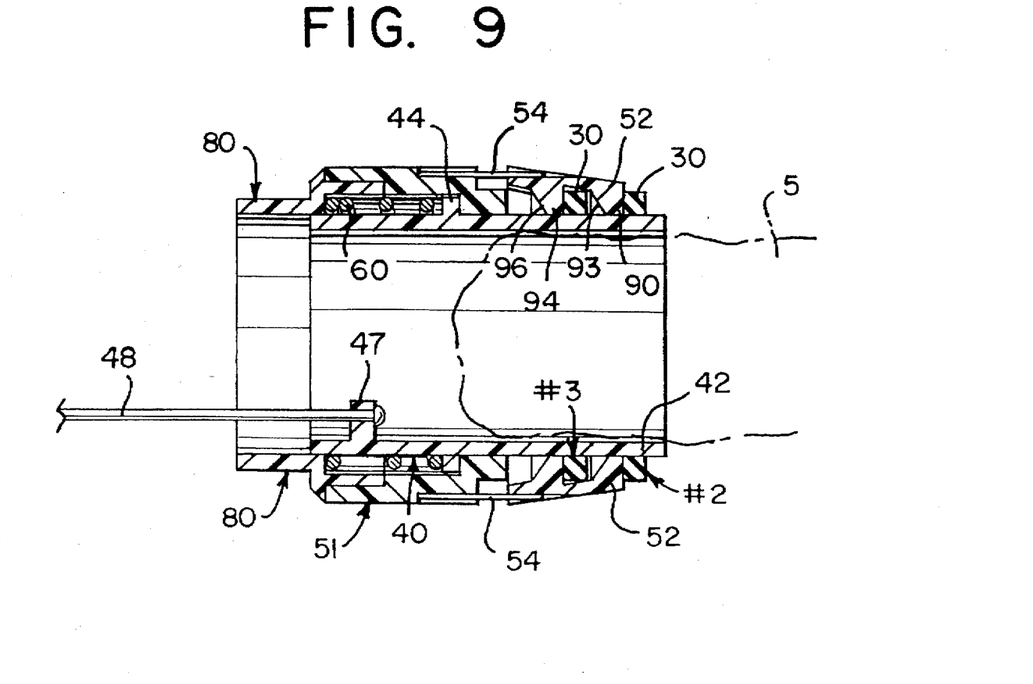
FIG. 9 is similar to FIG. 3, now showing the device after delivery of a first ligating band and after full relaxation of the coil spring, and with another body tissue portion placed within the reciprocating cylinder.

(the position formerly occupied by ligating ring no. 1). Similarly, ligating ring no. 3 will be moved, with respect to the proximal tooth 94 of spring fingers 52, to the position previously occupied by ligating ring no. 2. Upon full return of inner cylinder 40 to its distal-most position, the ligating device is ready for repeat use, as shown in FIG. 9.

Upon the next successive actuation of the ligating device, ring no. 2 will be dispensed. Upon the distal return of inner cylinder 40, however, this time there will only be one remaining ligating band (ring no. 3). The required splaying of spring fingers 52 is now caused by interference of ligating ring no. 3 with slopes surface 93 of distal tooth 90 of the spring fingers 52. While the spring fingers 52 of the presently illustrates embodiment are shown as including two teeth 90 and 94, it will be understood that spring fingers with greater numbers of teeth, such as three or four, or possibly more, could be employed as well. In each case, the number of ligating bands (N) which may be pre-loaded onto reciprocating inner cylinder 40 equals the number of teeth (T) plus one additional band (T+1) which starts in abutment with distal cap 51. If each spring finger 52 has four teeth, for example, the dispenser 18 can serially dispense five ligating bands.

Figure 10:
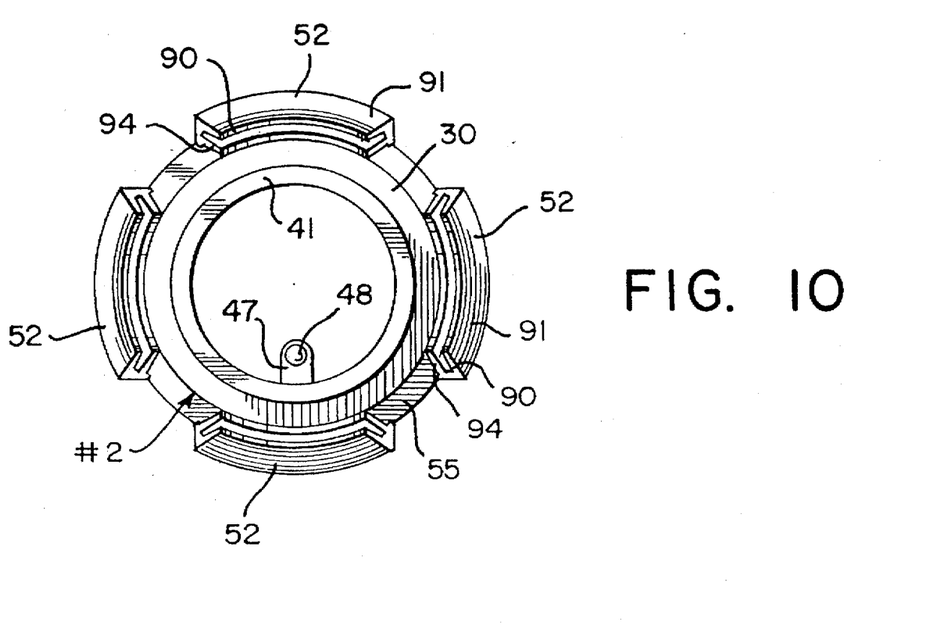
FIG. 10 is an end view of the dispenser in the operating state shown in cross section in FIG. 8, taken along line 10—10.

FIG. 10 is an end view of dispenser 18 in the condition shown in FIG. 8, taken along lines 10—10 in that figure. The ligating band 30 seen in this end view is ligating ring no. 2.

The embodiment shown in FIGS. 1 through 10 discloses a ligating band dispenser for a ligating instrument. The dispenser can dispense a single ligating band at a given location, or multiple ligating bands at a single location, or one or more bands at different locations. The surgeon may perform multiple ligating operations at different locations without having to withdraw the ligating instrument after each ligating band is dispensed.

Although this structure has been shown with respect to a particular ligating instrument 10, it will be apparent that a dispenser 18 constructed in accordance the disclosed embodiment is readily adapted for connection with a wide variety of structures including those based upon rigid or flexible endoscopic structures, as previously mentioned herein. It will also be apparent that this dispenser is reliable, readily producible and structurally sound. The use of a return coil spring 60 prevents premature dispensing of the ligating bands so that the requirement for the use of over tubes or separate stoppers is not required with ligating instruments incorporating this invention.

Other structures for providing the reciprocal, definite motion of the inner cylinder 40 could be substituted for the disclosed spring and trigger operating mechanism.

The ligating instrument is simple to use because it is merely necessary for the surgeon to position the ligating instrument and then actuate the trip wire 48. There is no need for the surgeon to sense the amount of travel required for depositing a single ligating band or a single set of ligating bands. The instrument is especially easy to operate because of the relatively low return force of the return spring 60 which is required to advance the ligating bands to their next successive positions on the reciprocating inner cylinder 40, and further because there is no necessity for further stretching the already relatively tightly stretched ligating rings in order to fife the device.

While this invention has been disclosed in terms of a particular embodiment and certain modifications, it will be apparent that many other modifications can be made to the specifically disclosed apparatus without departing from the invention. Therefore, it is the intent of the appended claims to cover all such variations and modifications as come within the true spirit and scope of this invention.

What is claimed is:

1. A ligating instrument for serially dispensing at least first and second elastic ligating bands onto at least one internal tissue site within a patient's body, comprising:

a hollow tubular housing having a proximal handle end and a distal end;

a ligating band dispenser mounted on the distal end of the housing, comprising:

a resiliently distally biased reciprocating inner cylinder having a distal portion adapted to support at least the first and second ligating bands in a stretched condition thereon, at first and second axial positions, respectively;

an axially fixed distal cap coaxially disposed on a proximal portion of the inner cylinder, the inner cylinder being axially movable relative to the distal cap; and a plurality of radially inwardly biased fingers connected to and extending distally from the distal cap, each of the fingers having at least first and second radially inwardly directed teeth having flat distal-facing surfaces and ramped proximal-facing surfaces, wherein the first axial position for the first ligating band is distal of the flat distal-facing surface of the first tooth, and the second axial position for the second ligating band is distal of the flat distal-facing surface of the second tooth and proximal of the ramped proximal-facing surface of the first tooth; and a trip wire connected to the inner cylinder and extending proximally through the housing to the proximal handle end, wherein proximal movement of the trip wire causes proximal movement of the inner cylinder so that the first ligating band is moved by the first tooth off of the inner cylinder from the first axial position, and the second ligating band is moved distally on the inner cylinder by the second tooth, and wherein upon subsequent distal biasing of the inner cylinder, the second ligating band causes the fingers to splay radially outwardly and then resiliently radially inwardly once the second ligating band moves distally of the flat distal-facing surface of the first tooth.

2. The ligating instrument of claim 1, further comprising:

a proximal cap connected to a proximal end of the distal cap, and enclosing therebetween a coil spring coaxially mounted on a proximal portion of the reciprocating inner cylinder, proximal of an outer flange thereon and separating the distal portion of the inner cylinder from the proximal portion, the flange limiting the distal movement of the inner cylinder with respect to the distal and proximal caps.

3. The ligating instrument of claim 1, further comprising:

means secured to the trip wire and positioned at the proximal handle end of the tubular housing for moving the trip wire proximally to cause dispensing of a ligating ring.

4. The ligating instrument of claim 2, wherein the reciprocating inner cylinder, distal cap and proximal cap are formed of a substantially transparent material.

5. The ligating instrument of claim 4, wherein the substantially transparent material is polycarbonate.

6. The ligating instrument of claim 1, wherein the inner cylinder distal portion is adapted to support a third ligating band in a stretched condition thereon, at a third axial position distal of and adjacent a flat distal-facing surface of the distal cap, and wherein proximal movement of the trip wire causes proximal movement of the inner cylinder so that the third ligating band is moved distally on the inner cylinder by the distal cap, and wherein upon subsequent distal biasing of the inner cylinder, the third ligating band causes the fingers to splay radially outwardly and then resiliently radially inwardly once the third ligating band moves distally of the flat distal-facing surface of the second tooth.

7. The ligating instrument of claim 1, wherein the inner cylinder distal portion is adapted to support a third ligating band in a stretched condition thereon, at a third axial position, each finger has a third radially inwardly directed tooth having flat distal-facing surfaces and ramped proximal-facing surfaces, the third axial position for the third ligating band is distal of the flat distal-facing surface of the third tooth, and wherein proximal movement of the trip wire causes proximal movement of the inner cylinder so that the third ligating band is moved distally on the inner cylinder by the third tooth, and wherein upon subsequent distal biasing of the inner cylinder, the third ligating band causes the fingers to splay radially outwardly and then resiliently radially inwardly once the third ligating band moves distally of the flat distal-facing surface of the second tooth.

8. The ligating instrument of claim 1, wherein the hollow tubular housing is a rigid introducer.

9. The ligating instrument of claim 1, wherein the hollow tubular housing is a flexible endoscope.

10. The ligating instrument of claim 1, further comprising:

means for drawing an internal tissue site within the distal portion of the reciprocating inner cylinder.

11. The ligating instrument of claim 1, wherein each of the fingers is connected to the distal cap by, and is also radially inwardly biased by, a flat spring attached to the distal cap and the finger.

12. The ligating instrument of claim 11, wherein the dispenser is relatively short in its overall axial dimension to thereby decrease the affect of tunnel vision.

13. The ligating instrument of claim 1, wherein the fingers are integrally connected to the distal cap by integrally formed radially inwardly biasing springs formed of the same material as the integral distal cap and the fingers.

14. The ligating instrument of claim 1, wherein the reciprocating inner cylinder and distal cap are formed of a substantially transparent material.

15. The ligating instrument of claim 14, wherein the substantially transparent material is polycarbonate.

* * * * *